United States Patent
Bourquin et al.

(10) Patent No.: US 12,220,505 B2
(45) Date of Patent: Feb. 11, 2025

(54) METHOD OF MONITORING AN OPERATION OF AN ELECTRIC BREAST PUMP

(71) Applicant: KONINKLIJKE PHILIPS N.V., Eindhoven (NL)

(72) Inventors: Yannyk Parulian Julian Bourquin, Eindhoven (NL); Jonathan Alambra Palero, Waalre (NL); Lili-Marjan Boelens-Brockhuis, Geldrop (NL); Okke Ouweltjes, Veldhoven (NL); Albertus Cornelis Den Brinker, Eindhoven (NL); Lucja Elzbieta Segaar, Oirschot (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1109 days.

(21) Appl. No.: 17/053,808

(22) PCT Filed: May 20, 2019

(86) PCT No.: PCT/EP2019/062907
§ 371 (c)(1),
(2) Date: Nov. 9, 2020

(87) PCT Pub. No.: WO2019/228834
PCT Pub. Date: Dec. 5, 2019

(65) Prior Publication Data
US 2021/0228788 A1  Jul. 29, 2021

(30) Foreign Application Priority Data
May 31, 2018 (EP) .................................. 18175349

(51) Int. Cl.
*A61M 1/06* (2006.01)

(52) U.S. Cl.
CPC .............. *A61M 1/06* (2013.01); *A61M 1/062* (2014.02); *A61M 1/0693* (2021.05); *A61M 1/0697* (2021.05); *A61M 2205/3327* (2013.01)

(58) Field of Classification Search
CPC ...... A61M 1/06; A61M 1/062; A61M 1/0693; A61M 1/0697; A61M 2205/3327; A61M 1/069

See application file for complete search history.

(56) References Cited

U.S. PATENT DOCUMENTS 3,705,516 A * 12/1972 Reis .................. G01H 1/003
73/659
2010/0094078 A1 4/2010 Weston
(Continued)

FOREIGN PATENT DOCUMENTS

WO 2016014488 1/2016

OTHER PUBLICATIONS

International Search Report and Written Opinion Dated Sep. 4, 2019 For International Application No. PCT/EP2019/062907 Filed May 20, 2019.
(Continued)

*Primary Examiner* — James D Ponton

(57) ABSTRACT

A method of monitoring an operation of an electric breast pump (100) using an external smart device (200) is provided. The external smart device (200) comprises a vibration detection unit (210) for detecting vibrations emitted from the breast pump (100). The detected vibrations are analyzed to extract information regarding the operation of the electric breast pump (100). The information comprises at least one of mode of operation and settings of the modes of operation of the breast pump (100). The extracted information can be outputted.

17 Claims, 2 Drawing Sheets

(56) References Cited

U.S. PATENT DOCUMENTS

| | | |
|---|---|---|
| 2010/0217148 A1 | 8/2010 | Binder |
| 2011/0004154 A1 | 1/2011 | Van Schijndel |
| 2012/0116298 A1* | 5/2012 | Van Schijndel ........ A61M 1/06 |
| | | 604/74 |
| 2016/0082166 A1 | 3/2016 | Guthrie |
| 2016/0183602 A1 | 6/2016 | Rider |
| 2016/0287767 A1 | 10/2016 | Simmons |
| 2017/0172485 A1 | 6/2017 | Makower |
| 2018/0104395 A1 | 4/2018 | Aalders |
| 2018/0228949 A1* | 8/2018 | Sablotsky ........... A61M 1/0697 |

OTHER PUBLICATIONS

Lansinoh, Smartpump 2.0 Double Electric Breast Pump https://lansinoh.com/products/smartpump2-double-electric-breast-pump.
Medela, Sonata Smart Breast Pump with PersonalFit Flex Breast Shields https://www.medela.us/breastfeeding/products/breast-pumps/sonata-smart-breast-pump-with-personalfit-flex-breast-shields.
YouTube Video, Different Breastpumps Noise Level Comparisons https://www.youtube.com/watch?v=bN_KLkVXlyo.

* cited by examiner

METHOD OF MONITORING AN OPERATION OF AN ELECTRIC BREAST PUMP

CROSS REFERENCE TO RELATED APPLICATIONS

This application is the U.S. National Phase application under 35 U.S.C. § 371 of International Application No. PCT/EP2019/062907 filed May 20, 2019, which claims the benefit of European Patent Application Number 18175349.2 filed May 31, 2018. These applications are hereby incorporated by reference herein.

FIELD OF THE INVENTION

The invention relates to a method of operating an electric breast pump, a smart device and a breast pump system.

BACKGROUND OF THE INVENTION

Breast pumps are used by breast feeding woman in order to extract milk such that this milk can be fed to the baby at a later time. Electric breast pumps typically have different settings or operation modes. A breast pump in particular has a stimulation phase and an expression phase during which the milk is expressed. The breast pump typically has a user interface through which the user can operate or control the breast pump. In particular, new users may not be completely familiar with the operation and different operation modes of a breast pump. Therefore, it is possible that less milk than expected can be expressed by means of the breast pump.

US 2016/0183602 A1 discloses a method of sound detection to differentiate data collected during the breast feeding of an infant and data collected during the use of a breast pump.

SUMMARY OF THE INVENTION

It is an object of the invention to provide a method of monitoring an operation of an electric breast pump which allows an easy and effective monitoring of the breast pump.

According to an aspect of the invention a method of monitoring an operation of an electric breast pump using an external smart device is provided. The external smart device comprises a vibration detection unit. Vibrations emitted from the breast pump are detected by the vibration detection unit. The detected vibrations are analyzed to extract information regarding the operation of the electric breast pump. The information comprises at least one of a mode of operation and settings of the modes of operation of the breast pump. The extracted information can be outputted.

According to the aspect of the invention it is possible to monitor an electric breast pump with an external device without having a connection to the breast pump. The breast pump does not need to be adapted in any kind. Thus, also existing breast pumps can be used according to an aspect of the invention.

According to an aspect of the invention the detected vibration is analyzed in an analyzing unit of the smart device. Thus, the analysis of the vibrations can be performed by the smart device without a need for example of an Internet connection.

According to a further aspect of the invention the analyzing step comprises comparing the detected vibration with pre-defined vibration patterns to determine information regarding the operation of the breast pump.

According to a further aspect of the invention a male functioning of the electric breast pump can be determine based on the detected vibration.

According to a further aspect of the invention the fitting of cups or funnels of the electric breast pump can be determine based on the detected vibration from the breast pump. Thus, it is possible to determine whether or not the cups or funnels of the breast pump which are pressed against the breast of a user have a good fit or not.

According to a further aspect of the invention the vibration detecting unit is implemented as a microphone. As smart devices such as smart phones, tablets, laptops, computers or the like typically have an inner microphone no further external devices are required. The vibration detection device can also be implemented as a velocity sensor, an accelerometer or a proximity sensor. As typical smart devices like smart phones, tablets comprise a velocity sensor or an accelerometer no additional external devices are required to monitor the operation of an electric breast pump.

According to a further aspect of the invention the detected settings or the detected modes of operation of the breast pump can be displayed for example on a display of the smart device in order to help the user to improve the expression of milk.

According to a further aspect of the invention in the analyzing step a spectral analysis of the detected vibrations of the electric breast pump can be performed and a temporal envelop of the vibrations in two frequency bands can be analyzed.

According to an aspect of the invention a smart device is provided which comprises a microphone configured to detect sound emitted by the breast pump. The smart device further more comprises an analyzing unit configured to analyze sound detected by the microphone to extract information regarding the operation of the electric breast pump. This information comprises at least one of a mode of operation or setting of the modes of operation of the breast pump.

According to an aspect of the invention a breast pump system comprising an electric breast pump and a smart device as described above is provided.

According to a further aspect of the invention a computer program for operating the smart device according to claim 6 is provided. The computer program comprises program code means for causing an analyzing unit in the smart device to carry out the method as defined in claim 1 when the computer program is run on the smart device.

The invention relates to the idea of using an external smart device which has a microphone to detect the sound of the breast pump during operation. Based on the detected sound the operation of the breast pump can be monitored, in particular, as different operating modes cause different sound or sound patterns. An analyzing unit in the smart device could analyze the sound pattern in order to determine the operating mode of the electric breast pump. In other words, based on the detected sound the operation of the breast pump can be analyzed and monitored. In particular, different pumping sound patterns of the breast pump can be detected and the detected sound can be used to extract information regarding settings of the breast pump (expression mode, duty cycle, sound frequency, etc.). Optionally, this information can be displayed on the smart device. The detected sound can be analyzed for example by means of spectral analysis in order to determine operation modes of the pump. Moreover, an information on proper "attachment" of the breast pump expression kit to the breast can be derived from the sound data (e.g. loose of vacuum). This feedback could be given to the user to provide the most efficient expression.

According to an aspect of the invention the operation of a breast pump can be monitored by an external smart device which does not need a connectivity like wireless connectivity to the breast pump. In particular, the sound of the breast pump is detected and analyzed by the external smart device. Operational setting and operational modes of the breast pump are derived from the detected sound. Thus, the method of monitoring operation of a breast pump according to an aspect of the invention is advantageous as no additional hardware is required in the breast pump and as no physical connectivity must be present between the breast pump and the smart device. Thus, the method of monitoring the operation of a breast pump can also be used for already existing breast pumps.

The smart device can be a smart phone, a tablet, a smart wearable, e.g. a smart watch or a computer as long as they have a microphone or are coupled to a microphone and are able to analyze data. In the analyzing unit an algorithm is used to analyze the sound recorded by the microphone. The analyzing unit can also be implemented as an application running on the smart device.

According to an aspect of the invention the smart device may store information on the operational settings and operation of a smart device. This information may be obtained via the application running on the smart device. For this, for example, the user may input the name and make of or product number the breast pump and the smart device may access a data base via the internet to extract breast pump specific sound pattern. These sound patterns can then be stored on the smart device and may be used during the analysis of the detected sound. Accordingly, these sound patterns are predefined sound patterns. Alternatively, the application running on the smart device can recognize the breast pump from itself based on the detected sound.

Based on the extracted information regarding the operation of a breast pump the smart device may determine or detect a milk extraction behavior of a user.

It shall be understood that a preferred embodiment of the present invention can also be any combination of the dependent claims or above embodiments or aspects of the respective independent claims.

These and other aspects of the invention will be apparent from and elucidated with reference to the embodiments described hereinafter.

DETAILED DESCRIPTION OF EMBODIMENTS

Figure 1:
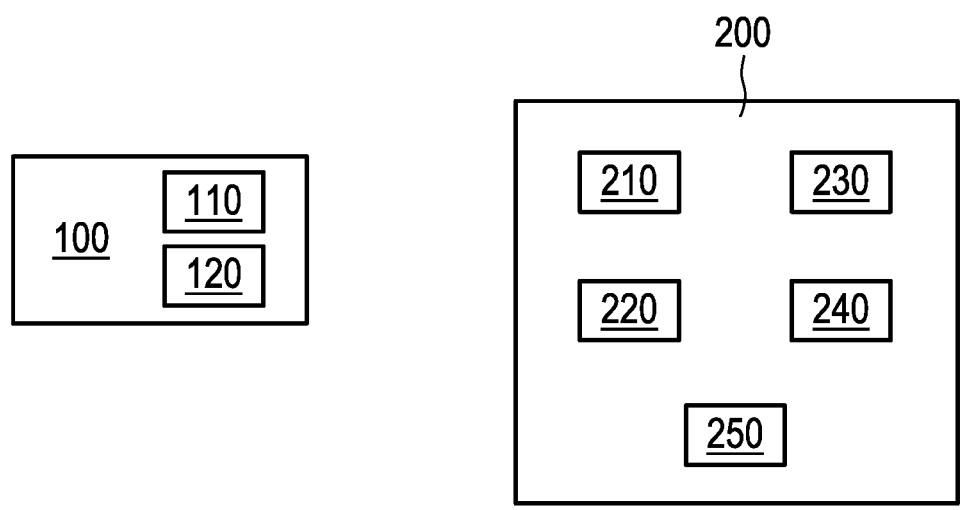
FIG. 1 shows a schematic block diagram of a breast pump as well as a smart device according to an aspect of the invention.

FIG. 1 shows a schematic block diagram of a breast pump as well as a smart device according to an aspect of the invention. The electric breast pump 100 is used by a user for extracting milk. The breast pump 100 comprise a pump 110 which is used for creating a vacuum in order to express milk and cups or funnels 120 which can be pressed against the breast of the user.

The smart device 200 can be placed in the proximity of the breast pump 100. The smart device 200 comprises at least one vibration detection unit like a microphone 210 and an analyzing unit 220. Optionally, the smart device 200 can comprise a display 230 as well as a wireless communication unit 240 and a processing unit 250 which can be adapted to run applications which can be stored on the smart device.

In order to monitor the operation of the breast pump 100 the smart device 200 can be placed in the vicinity of the breast pump and the at least one microphone 210 is activated to detect sound from the breast pump.

The sound of the breast pump 100 detected by the microphone 110 (or the vibration detected by the vibration detection unit) is analyzed in the analyzing unit 220. The analyzing unit 220 may also be part of the processing unit 250. An algorithm can be used in the analyzing unit 220 to analyze the detected sounds in order to extract information regarding the operation or mode of operation and the setting of the mode of operation of the breast pump. The breast pump 100 can have several modes of operation like expression modes (e.g. a first, second and third expression mode E1, E2, E3 and a stimulation mode S. Based on the detected sound the analyzing unit 220 analyses the sound in order to determine which of the modes of operation and optionally which settings of the modes of operation are used by the breast pump. The different settings of the modes of operation can for example be the duty cycle, the vacuum, the cycle time and the time to vacuum.

The above mentioned settings (like the vacuum, the cycle time and the time to vacuum) of the different modes can be as follows:

| # | Mode | Max Vac [mbar] | | Cycle Time [s] | | Time To Vac [s] | |
|---|---|---|---|---|---|---|---|
| | | Mean | Std | Mean | Std | Mean | Std |
| 1 | Stimulation S | −170 | | 0.600 | | 0.4 | |
| 2 | Expression I E1 | −225 | | 1.250 | | 0.775 | |
| 3 | Expression II E2 | −279 | | 1.275 | | 0.85 | |
| 4 | Expression III E3 | −333 | | 1.320 | | 0.90 | |

Optionally, the analyzing unit 220 may use predetermined or pre-defined sound patterns or sound features which are unique to specific breast pump in order to determine which of the operational settings are used by the breast pump. The pre-defined sound patterns can for example be forwarded to the smart device via the wireless communication unit 240.

According to an aspect of the invention, the settings of the breast pump can be slightly modified (e.g. a slightly longer duty cycle) to improve the distinguishability of the different modes of operation (expression mode, stimulation mode) and the different settings of the modes of operation. However, care must be taken, that the efficiency of the pump does not suffer too much.

Optionally, the detected modes of operation and/or the detected settings can be displayed on the display 230.

Figure 2:
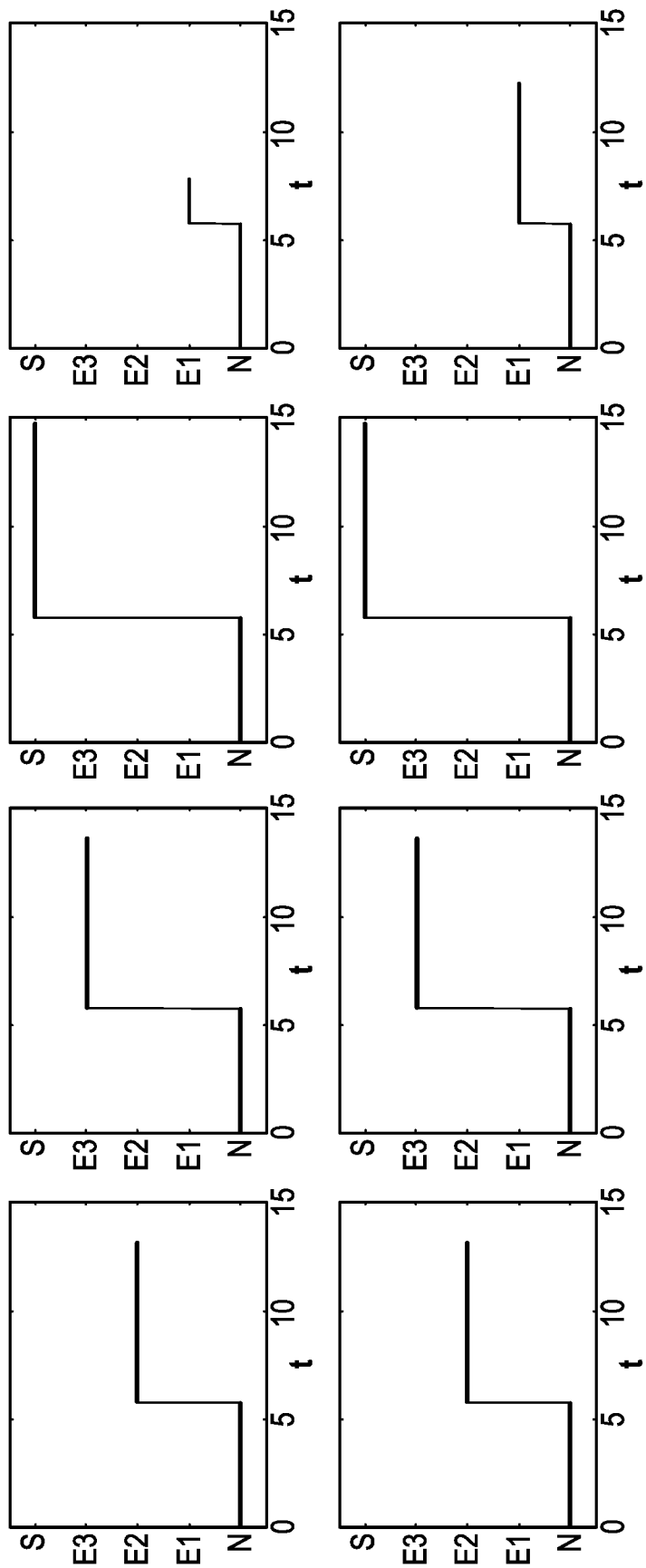
FIG. 2 shows a graph depicting different settings of the breast pump detected by the smart device.

FIG. 2 shows a graph depicting different settings of the breast pump detected by the smart device. In FIG. 2 the results of operational settings of the breast pump as detected by the microphone of the smart device are depicted over time t. In the first graph, after six seconds, the second expression operating mode E2 is detected. In the next graph, the third expression operation mode E3 is detected. In the third graph, the stimulation operating mode S is detected. In the fourth graph, the first expression operating mode E1 is detected. The lower graphs substantially correspond to the upper graphs.

The smart device in particular the analyzing units 220 may also detect the time during which the breast pump is in a specific operating mode like the stimulation mode or the expression mode.

Based on the detected operating settings and operating mode of the breast pump information can be displayed on the display 230 in order to help the user to improve the expression of milk. For example, if the user is in the simulation mode for longer time (e.g. greater than 3 min) the smart device may display information regarding the importance of relaxation for milk expression. Furthermore, this may also include advise to relax or provide relaxing sound or music.

The information detected by the smart device 200 may also be gathered over several days or weeks in order to determine the routine of the user. Based on this information the smart device can remind the user of a time for a further milk expression.

Furthermore, on the smart device also a calendar application may be running. The information of this calendar app can be incorporated into the advice given to the user of the breast pump 100 and the smart device 200. In particular, the smart device 200 may help the user to plan expression sessions based on the time of previous milk expression, breast feeding sessions at a preferred amount of time between these sessions as well as the information or appointments in the calendar on the smart device.

The smart device may also have a camera which can be used to detect an amount of milk extracted by means of the breast pump. For this, the user may only need to take a photo of the milk inside a bottle of the breast pump.

The smart device may also log the amount of milk, the timings and duration of the expression sessions, the settings of the breast pump as well as the extracted milk volume in order to increase the extracted milk volume.

The application run on the smart device may also detect the routine of a user, for example, expressing once in the morning and twice in the afternoon and that she is expressing more milk in the morning than in the afternoon. This could be used to provide more inside on the woman's milk production which may be increased during a morning then during the afternoon. This information can be used to give an advice for example to express twice in the morning rather than twice in the afternoon.

According to an aspect of the invention the application may be used to track the use of the breast pump by the user in order to determine whether the user has followed the advice of the application.

According to a further aspect of the invention the detecting information as well as the analysis of the analyzing unit can be displayed on the display 230. This information's may include information regarding the speed of the extraction, the amount of extraction etc. In particular, these may include the information "you expressed the same amount of milk using setting 2 as 3, but are faster when using setting 3". Or it may also include "if you want to be comfortable, you can express using setting 2 and you will have enough milk for your baby, but if you want to be done fast, you can use setting 3 and save x minutes in expression time".

Moreover, the application and the smart device can be able to detect an end of the pumping session and to trigger additional events. For example, if the user is finished with extracting milk, the user may take a picture of the milk inside the bottle in order to determine how much milk was expressed.

According to a further aspect of the invention the application running on the smart device may determine whether a funnel of the breast pump has been correctly attached to the breast. If the cup or funnel is completely sealing the breast, the pump will need more effort to create the volume. This will lead to a greater loading on the motor of the pump and thus to a slower revolution of the pump. This can be detected by the sounds emitted by the pump unit 110. The analyzing unit 220 may use temple-spectra analyses to detect this change and the rotational frequency. This information may be used to determine whether or not the breast is correctly sealed by the funnel or cup.

According to a further aspect of the invention the smart device may also determine when the pump is defect or has a failure as this will lead to different sound.

Furthermore, the algorithm used by the analyses unit 220 can be a machine learning algorithm like a deep neutral network. According to an aspect of the invention a spectral analysis of the detected sound of the breast pump can be performed. In particular, the temporal envelope of the sound in two frequency bands at 6.82-8 kHz and at 19.9 kHz can be analyzed as these two frequency bands may contain specific information for each operating mode of the breast pump. Optionally, frames of 5.8 seconds can be taken using these two frequency ranges. An average of 2 auto-correlation function can be performed from smoothed and windowed energy profiles. A lag for the auto-correlation may correspond to the cycle time of the pumping profile.

According to an aspect of the invention, a vibration detection unit may be used to detect vibrations of the electric breast pump. The vibration detection unit can be embodied as a microphone as described above.

Alternatively, the vibrations detection unit can be embodied as an accelerometer a velocity sensor or a proximity sensor (e.g. inside the smart device). If the smart device is placed on the electric breast pump, the accelerometer can detect the vibration of the breast pump and can analyze the vibration as described above.

Other variations of the disclosed embodiment can be understood and effected by those skilled in the art in practicing the claimed invention from a study of the drawings, the disclosure and the appended claims.

In the claims, the word "comprising" does not exclude other elements or steps and in the indefinite article "a" or "an" does not exclude a plurality.

A single unit or device may fulfil the functions of several items recited in the claims. The mere fact that certain measures are recited in mutual different dependent claims does not indicate that a combination of these measurements cannot be used to advantage. A computer program may be stored/distributed on a suitable medium such as an optical storage medium or a solid state medium, supplied together with or as a part of other hardware, but may also be distributed in other forms such as via the internet or other wired or wireless telecommunication systems.

Any reference signs in the claims should not be construed as limiting the scope.

The invention claimed is:

1. A method of monitoring an operation of an electric breast pump using an external smart device having a vibration detection unit, the method comprising:
   detecting vibrations emitted from the electric breast pump by the vibration detection unit of the external smart device capturing sound from the electric breast pump;

analyzing the detected vibrations to extract information regarding operation of the electric breast pump;
wherein the information comprises at least one of a mode of operation, and settings of modes of operation of the electric breast pump, and
outputting the extracted information,
wherein the detected vibrations are analyzed in an analyzing unit of the external smart device,
wherein the analyzing comprises comparing the detected vibrations with pre-defined vibration patterns to determine information regarding operation of the electric breast pump, and
wherein, in the analyzing, a spectral analysis of the detected vibrations of the electric breast pump is performed, and a temporal envelope of the detected vibrations in two frequency bands is analyzed.

2. The method of monitoring an operation of an electric breast pump according to claim 1, further comprising:
determining a malfunction of the electric breast pump based on the detected vibrations of the electric breast pump.

3. The method of monitoring an operation of an electric breast pump according to claim 1, further comprising:
determining a fit of cups or funnels of the electric breast pump based on the detected vibrations from the electric breast pump.

4. The method of monitoring an operation of an electric breast pump according to claim 1,
wherein the vibration detection unit is a microphone.

5. The method of monitoring an operation of a breast pump according to claim 1,
wherein mode of operation or settings of modes of operation of the electric breast pump are displayable in order to help a user to improve expression of milk.

6. The method of monitoring an operation of an electric breast pump according to claim 1, wherein the smart device is not connected to the electric breast pump.

7. A tangible, non-transitory computer readable medium that stores a computer program for operating the external smart device as in claim 1, wherein the computer program comprises program code for causing an analyzing unit to carry out the method as defined in claim 1, when the computer program is run on the external smart device as in claim 1.

8. A smart device, comprising
a vibration detection unit configured to detect vibrations emitted from a breast pump by capturing sound from the breast pump; and
an analyzing unit configured to analyze vibrations detected by the vibration detection unit to determine information regarding operation of the breast pump by comparing the detected vibrations with pre-defined vibration patterns and by performing spectral analysis of the detected vibrations, and by analyzing a temporal envelope of the detected vibrations in two frequency bands;
wherein the information comprises at least one of a mode of operation or settings of modes of operation of the breast pump.

9. The smart device of claim 8, wherein the smart device is not connected to the breast pump.

10. A breast pumping system, comprising an electric breast pump, and a smart device according to claim 8.

11. A breast pump monitor, comprising
a vibration detector configured to detect vibrations emitted from a breast pump by capturing sound from the breast pump; and
an analyzer configured to analyze vibrations detected by the vibration detector to determine information regarding operation of the breast pump by comparing the detected vibrations with pre-defined vibration patterns;
wherein the information comprises at least one of a mode of operation or settings of modes of operation of the breast pump.

12. The breast pump monitor of claim 11,
wherein the analyzer is further configured to perform a spectral analysis of the detected vibrations.

13. The breast pump monitor of claim 11,
wherein the analyzer is further configured to analyze a temporal envelope of the detected vibrations in two frequency bands.

14. The breast pump monitor of claim 11,
wherein the analyzer is further configured to determine a malfunction of the breast pump based on the detected vibrations of the breast pump.

15. The breast pump monitor of claim 11,
wherein the analyzer is further configured to determine a fit of cups or funnels of the breast pump based on the detected vibrations from the breast pump.

16. The breast pump monitor of claim 11, further comprising:
a display wherein the settings or the mode of operation determined by the analyzer are displayed on the display.

17. The breast pump monitor of claim 11, wherein the breast pump monitor is not connected to the breast pump.

* * * * *